United States Patent
Seok et al.

(10) Patent No.: US 11,791,052 B2
(45) Date of Patent: Oct. 17, 2023

(54) METHOD FOR ESTIMATING MENTAL HEALTH AND PROVIDING SOLUTION FOR MENTAL HEALTH BY LEARNING PSYCHOLOGICAL DATA AND PHYSICAL DATA BASED ON MACHINE LEARNING AND MENTAL HEALTH ESTIMATING DEVICE USING THE SAME

(71) Applicants: MINDSAI CO., LTD., Seoul (KR); INDUSTRY-ACADEMIC COOPERATION FOUNDATION, YONSEI UNIVERSITY, Seoul (KR)

(72) Inventors: Jeong Ho Seok, Seongnam-Si (KR); Su A. Jang, Seoul (KR); Sun Woo Choi, Seoul (KR); Tae Jung Kim, Busan (KR); Chang Hyun Kim, Seoul (KR); Ryun Sup Ahn, Gwangju (KR)

(73) Assignees: MINDSAI CO., LTD., Seoul (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 17/876,962

(22) Filed: Jul. 29, 2022

(65) Prior Publication Data
US 2022/0367065 A1 Nov. 17, 2022

Related U.S. Application Data

(63) Continuation of application No. PCT/KR2021/007556, filed on Jun. 16, 2021.

(30) Foreign Application Priority Data

Feb. 4, 2021 (KR) .................. 10-2021-0016379

(51) Int. Cl.
*G16H 50/30* (2018.01)
*G06N 20/00* (2019.01)
*G01N 33/53* (2006.01)
*G01N 33/74* (2006.01)

(52) U.S. Cl.
CPC .............. *G16H 50/30* (2018.01); *G01N 33/53* (2013.01); *G01N 33/74* (2013.01); *G06N 20/00* (2019.01)

(58) Field of Classification Search
CPC ........ G16H 50/30; G06N 20/00; G01N 33/53; G01N 33/74
See application file for complete search history.

(56) References Cited

U.S. PATENT DOCUMENTS

| | | | |
|---|---|---|---|
| 11,315,041 B1 * | 4/2022 | Jain | G06N 20/20 |
| 2019/0244127 A1 | 8/2019 | Amado et al. | |
| 2021/0295207 A1 | 9/2021 | Neumann | |

FOREIGN PATENT DOCUMENTS

| | | |
|---|---|---|
| JP | 2018-181004 A | 11/2018 |
| KR | 10-2017-0006919 A | 1/2017 |
| KR | 101911516 B1 | 10/2018 |
| KR | 10-2020-0025756 A | 3/2020 |
| KR | 10-2020-0038628 A | 4/2020 |
| KR | 1020200134098 | 12/2020 |
| KR | 10-2254481 | 5/2021 |

OTHER PUBLICATIONS

Office Action, Canadian Application No. 3,169,245, dated Mar. 1, 2023 (6 pages).
Office Action, Japanese Patent Application No. 2022-546498, dated Feb. 6, 2023 (3 pages).
Hagad et al., "Modeling Work Stress Using Heart Rate and Stress Coping Profiles," SAT 2015 18th International Conference, Austin TX, Sep. 24-27, 2015, vol. 9935, Chap. 9, No. 558, pp. 108-118, Dec. 1, 2016.
Zhang et al., "A Deep Temporal Model for Mental Fatigue Detection," 2018 IEEE International Conference on Systems, Man, and Cybernetics (SMC), IEEE pp. 1879-1884, Oct. 7, 2018.
Extended European Search Report, European Application No. 21923591. 8, dated Jul. 25, 2023 (13 pages).

* cited by examiner

*Primary Examiner* — Jerry Lin
(74) *Attorney, Agent, or Firm* — Occhiuti & Rohlicek LLP (57) ABSTRACT

The method for estimating mental health and providing solution for mental health by learning psychological data and biological data based on machine learning includes: (a) acquiring, by mental health estimating device, psychological data for testing and biological data for testing of test subject from terminal of the test subject in state in which first estimated model is learned by referring to estimated mental health data for learning output from the first estimated model and ground truth mental health data corresponding to the estimated mental health data after psychological data for learning and biological data for learning of learning subjects are input to the first estimated model; and (b) inputting, by the mental health estimating device, the psychological data for testing and the biological data for testing to the first estimated model to allow the first estimated model to output estimated mental health data for testing.

26 Claims, 5 Drawing Sheets

METHOD FOR ESTIMATING MENTAL HEALTH AND PROVIDING SOLUTION FOR MENTAL HEALTH BY LEARNING PSYCHOLOGICAL DATA AND PHYSICAL DATA BASED ON MACHINE LEARNING AND MENTAL HEALTH ESTIMATING DEVICE USING THE SAME

CROSS REFERENCE TO RELATED APPLICATIONS

This application is a continuation of International Application no. PCT/KR2021/007556, filed Jun. 16, 2021, which claims the benefit of the filing date of Korean Application No. 10-2021-0016379, filed Feb. 4, 2021, the contents of which are hereby incorporated by reference in their entirety.

TECHNICAL FIELD

The present disclosure relates to a method for estimating mental health and providing a solution for mental health and a mental health estimating device using the same, and more particularly, to a method for estimating mental health and providing a solution for mental health by learning psychological data and biological (or physical) data based on machine learning and a mental health estimating device using the same.

BACKGROUND ART

Mental illnesses including depression or the like have various aspects, so it is difficult to determine mental health of a mild or severe case in comparison with healthy people.

In addition, since a solution for mental health suitable for each patient with a mild or severe case is different, it is difficult to select and provide a specific solution for mental health that includes various psychological treatment processes and various drug treatment processes suitable for each patient.

For example, there is a difference in that, for patients with mild depression, symptoms may be improved only by drug treatment or only by psychotherapy, whereas, for patients with severe depression, symptoms may be improved only when drug treatment and psychotherapy are applied together. However, there is a problem in that it is difficult to determine which patient should be provided with drug and psychological treatment and to what extent.

Accordingly, there is a need for an improved method for solving the above problems.

DISCLOSURE

Technical Problem

The present disclosure aims to solve all of the above problems.

In addition, the present disclosure provides estimating mental health of a test subject by learning biological (or physical) and psychological data of healthy people and patients based on machine learning.

In addition, the present disclosure provides a suitable solution for mental health to a test subject based on estimated mental health data for the test subject.

Technical Solution

In order to achieve the objects of the present disclosure as described above and to realize the characteristic effects of the present disclosure to be described later, the characteristic configuration of the present disclosure is as follows.

According to an aspect of the present invention, a method for estimating mental health and providing a solution for mental health by learning psychological data and biological (or physical) data based on machine learning and a mental health estimating device using the same includes: (a) acquiring, by a mental health estimating device, psychological data for testing and biological data for testing of a test subject from a terminal of the test subject in a state in which a first estimated model is learned by referring to estimated mental health data for learning output from the first estimated model and ground truth (GT) mental health data corresponding to the estimated mental health data for learning after psychological data for learning and biological data for learning of a plurality of learning subjects are input to the first estimated model; and (b) inputting, by the mental health estimating device, the psychological data for testing and the biological data for testing to the first estimated model to allow the first estimated model to output estimated mental health data for testing.

The first estimated model includes a 1_1th estimated model, a 1_2th estimated model and a 1_3th estimated model, in the (a), (i) after 1_1th psychological data for learning including at least a part of 1_1th positive psychological information for learning and 1_1th negative psychological information for learning of the learning subject is input to the 1_1th estimated model, by referring to 1_1th estimated mental health data for learning output from the 1_1th estimated model and 1_1th GT mental health data corresponding to the 1_1th estimated mental health data, the 1_1th estimated model is learned, (ii) after the 1_1th estimated mental health data for learning or the 1_1th GT mental health data, and 1_2th learning psychological data including at least a part of 1_2th positive psychological information for learning and 1_2th negative psychological information for learning of the learning subject is input to the 1_2th estimated model, by referring to the 1_2th estimated mental health data for learning output from the 1_2th estimated model and 1_2th GT mental health data corresponding to the 1_2th estimated mental health data for learning, the 1_2th estimated model is learned, and (iii) after the 1_2th estimated mental health data for learning or the 1_2th GT mental health data, and the biological data for learning are input to the 1_3th estimated model, by referring to the 1_3th estimated mental health data for learning output from the 1_3th estimated model and 1_3th GT mental health data corresponding to the 1_3th estimated mental health data for learning, in a state in which the 1_3th estimated model is learned, the mental health estimating device acquires 1_1th psychological data for testing, 1_2th psychological data for testing, and the biological data for testing of the test subject from the terminal of the test subject, and in the (b), the mental health estimating device (i) inputs the 1_1th psychological data for testing to the 1_1th estimated model to allow the 1_1th estimated model to output 1_1th estimated mental health data for testing, (ii) inputs the 1_1th estimated mental health data for testing and the 1_2th psychological data for testing to the 1_2th estimated model to allow the 1_2th estimated model to output 1_2th estimated mental health data for testing, and (iii) inputs the 1_2th estimated mental health data for testing and the biological data for testing to the 1_3th estimated model to allow the 1_3th estimated model to output 1_3th estimated mental health data for testing.

The biological data for learning includes a hormone concentration value for learning of the learning subject, and the biological data for testing includes a hormone concentration value for testing of the test subject, and in the (a), after the 1_2th estimated mental health data for learning or the 1_2th GT mental health data, and the biological data for learning including the hormone concentration value for learning of the learning subject are input to the 1_3th estimated model, by referring to the 1_3th estimated mental health data for learning output from the 1_3th estimated model and the 1_3th GT mental health data, the 1_3th estimated model is learned.

The hormone concentration value for learning includes a Cortisol concentration value for learning and a dehydroepiandrosterone (DHEA) concentration value for learning, and the hormone concentration value for testing includes a Cortisol concentration value for testing and a DHEA concentration value for testing.

The hormone concentration value for learning further includes a sex hormone concentration value for learning, and the hormone concentration value for testing further includes a sex hormone concentration value for testing, and in the (a), when the sex hormone concentration value for learning meets a threshold range, in a state in which a first weight applied to the 1_1th positive psychological information for learning and the 1_2th positive psychological information for learning is set to be smaller than a second weight applied to the 1_1th negative psychological information for learning and the 1_2th negative psychological information for learning, the 1_1th estimated model to the 1_3th estimated model are learned.

By analyzing (i) first saliva for learning to fourth saliva for learning sampled at a first sampling time for learning to a third sampling time for learning that exists within a first threshold time range from a time when the learning subject wakes up, and at a fourth sampling time for learning that exists within a second threshold time range from a time when the learning subject goes to sleep, and (ii) first saliva for testing to fourth saliva for testing sampled at a first sampling time for testing to a third sampling time for testing that exists within the first threshold time range from the time when the test subject wakes up and at a fourth sampling time for testing that exists within the second threshold time range from the time when the test subject goes to sleep, respectively, each of the hormone concentration value for learning and the hormone concentration value for testing is calculated.

The hormone concentration value for learning and the hormone concentration value for testing are respectively calculated by analyzing each of the first saliva for learning to the fourth saliva for learning and the first saliva for testing to the fourth saliva for testing through a radioimmunoassay.

The biological data for learning includes a heart rate variability value for learning of the learning subject, and the biological data for testing includes a heart rate variability value for testing of the test subject, and in the (a), after the 1_2th estimated mental health data for learning or the 1_2th GT mental health data, and the biological data for learning including the heart rate variability value for learning of the learning subject are input to the 1_3th estimated model, by referring to the 1_3th estimated mental health data for learning output from the 1_3th estimated model and the 1_3th GT mental health data, the 1_3th estimated model is learned.

The biological data for learning includes brain image data for learning and microbiome data for learning of the learning subject, and the biological data for testing includes brain image data for testing and microbiome data for testing of the test subject, and in the (a), after the 1_2th estimated mental health data for learning or the 1_2th GT mental health data, and the biological data for learning including the brain image data for learning and the microbiome data for learning of the learning subject are input to the 1_3th estimated model, by referring to the 1_3th estimated mental health data for learning output from the 1_3th estimated model and the 1_3th GT mental health data, the 1_3th estimated model is learned.

The 1_1th psychological data for learning includes adult attachment type information for learning, adverse childhood experiences information for learning, and mind understanding ability information for learning of the learning subject, the 1_2th psychological data for learning includes depression scale information for learning and suicide risk information for learning of the learning subject, the 1_1th psychological data for testing includes adult attachment type information for testing, adverse childhood experiences information for testing, and mind understanding ability information for testing of the test subject, and the 1_2th psychological data for testing includes depression scale information for testing and suicide risk information for testing of the test subject, and in the (a), (i) after the 1_1th psychological data for learning including the adult attachment type information for learning, the adverse childhood experiences information for learning, and the mind understanding ability information for learning is input to the 1_1th estimated model, by referring to the 1_1th estimated mental health data for learning output from the 1_1th estimated model and the 1_1th GT mental health data corresponding to the 1_1th estimated mental health data for learning, the 1_1th estimated model is learned, and (ii) after the 1_1th estimated mental health data for learning or the 1_1th GT mental health data, and the 1_2th psychological data for learning including the depression scale information for learning and the suicide risk information for learning are input to the 1_2th estimated model, by referring to the 1_2th estimated mental health data for learning output from the 1_2th estimated model and the 1_2th GT mental health data corresponding to the 1_2th estimated mental health data for learning, the 1_2th estimated model is learned.

At least a part of the 1_1th psychological data for learning and the 1_2th psychological data for learning further includes recovery resilience information for learning of the learning subject, and at least a part of the 1_1th psychological data for testing and the 1_2th psychological data for testing further includes recovery resilience information for testing of the test subject.

In the (a), (i) after the psychological data for learning and the biological data for learning of the learning subject are input to the first estimated model, by referring to the estimated mental health data for learning output from the first estimated model and the GT mental health data, the first estimated model is learned, and (ii) after the estimated mental health data for learning or the GT mental health data is input to the second estimated model, by referring to (ii-1) post-treatment estimated mental health data for learning of the learning subject whose mental health status has been changed by applying at least a part of the drug treatment process and the psychotherapy process to the learning subject, (ii-2) estimated drug treatment data for learning for the drug treatment process, and (ii-3) estimated psychotherapy data for learning for the psychotherapy process, which are output from the second estimated model, and post-treatment GT mental health data, GT drug treatment data, and GT psychotherapy data corresponding to each of them, in a state in which the second estimated model is learned, the mental health estimating device acquires the psychological data for testing and the biological data for testing of the test subject from the terminal of the test subject, and in the (b), the mental health estimating device inputs the psychological data for testing and the biological data for testing to the first estimated model to allow the first estimated model to output the estimated mental health data for testing, and the method further includes (c) providing, by the second estimated model, a specific solution for mental health that includes estimated drug treatment data for testing and estimated psychotherapy data for testing for a specific psychotherapy process for a specific drug treatment process, which are to be applied to the test subject during the drug treatment process and the psychotherapy process, by inputting the estimated mental health data for testing by the mental health estimating device to the second estimated model.

A mental health estimating device for estimating mental health and providing a solution for mental health by learning psychological data and biological data based on machine learning includes: at least one memory configured to store instructions; and at least one processor configured to execute the instructions, wherein (1) the processor performs a process of acquiring psychological data for testing and biological data for testing of a test subject from a terminal of the test subject in a state in which a first estimated model is learned by referring to estimated mental health data for learning output from the first estimated model and GT mental health data corresponding to the estimated mental health data for learning after psychological data for learning and biological data for learning of a plurality of learning subjects are input to the first estimated model, and (2) performs a process of inputting the psychological data for testing and the biological data for testing to the first estimated model to allow the first estimated model to output estimated mental health data for testing.

The first estimated model includes a 1_1th estimated model, a 1_2th estimated model and a 1_3th estimated model, and in the process (1), (i) after 1_1th psychological data for learning including at least a part of 1_1th positive psychological information for learning and 1_1th negative psychological information for learning of the learning subject is input to the 1_1th estimated model, by referring to 1_1th estimated mental health data for learning output from the 1_1th estimated model and 1_1th GT mental health data corresponding to the 1_1th estimated mental health data, the 1_1th estimated model is learned, (ii) after the 1_1th estimated mental health data for learning or the 1_1th GT mental health data, and 1_2th learning psychological data including at least a part of 1_2th positive psychological information for learning and 1_2th negative psychological information for learning of the learning subject is input to the 1_2th estimated model, by referring to the 1_2th estimated mental health data for learning output from the 1_2th estimated model and 1_2th GT mental health data corresponding to the 1_2th estimated mental health data for learning, the 1_2th estimated model is learned, and (iii) after the 1_2th estimated mental health data for learning or the 1_2th GT mental health data, and the biological data for learning are input to the 1_3th estimated model, by referring to the 1_3th estimated mental health data for learning output from the 1_3th estimated model and 1_3th GT mental health data corresponding to the 1_3th estimated mental health data for learning, in a state in which the 1_3th estimated model is learned, the processor acquires 1_1th psychological data for testing, 1_2th psychological data for testing, and the biological data for testing of the test subject from the terminal of the test subject, and in the process (2), the processor (i) inputs the 1_1th psychological data for testing to the 1_1th estimated model to allow the 1_1th estimated model to output 1_1th estimated mental health data for testing, (ii) inputs the 1_1th estimated mental health data for testing and the 1_2th psychological data for testing to the 1_2th estimated model to allow the 1_2th estimated model to output 1_2th estimated mental health data for testing, and (iii) inputs the 1_2th estimated mental health data for testing and the biological data for testing to the 1_3th estimated model to allow the 1_3th estimated model to output 1_3th estimated mental health data for testing.

The biological data for learning includes a hormone concentration value for learning of the learning subject, and the biological data for testing includes a hormone concentration value for testing of the test subject, and in the process (1), after the 1_2th estimated mental health data for learning or the 1_2th GT mental health data, and the biological data for learning including the hormone concentration value for learning of the learning subject are input to the 1_3th estimated model, by referring to the 1_3th estimated mental health data for learning output from the 1_3th estimated model and the 1_3th GT mental health data, the 1_3th estimated model is learned.

The hormone concentration value for learning includes a Cortisol concentration value for learning and a dehydroepiandrosterone (DHEA) concentration value for learning, and the hormone concentration value for testing includes a Cortisol concentration value for testing and a DHEA concentration value for testing.

The hormone concentration value for learning further includes a sex hormone concentration value for learning, and the hormone concentration value for testing further includes a sex hormone concentration value for testing, and in the process (1), when the sex hormone concentration value for learning meets a threshold range, in a state in which a first weight applied to the 1_1th positive psychological information for learning and the 1_2th positive psychological information for learning is set to be smaller than a second weight applied to the 1_1th negative psychological information for learning and the 1_2th negative psychological information for learning, the 1_1th estimated model to the 1_3th estimated model are learned.

By analyzing (i) first saliva for learning to fourth saliva for learning sampled at a first sampling time for learning to a third sampling time for learning that exists within a first threshold time range from a time when the learning subject wakes up, and at a fourth sampling time for learning that exists within a second threshold time range from a time when the learning subject goes to sleep, and (ii) first saliva for testing to fourth saliva for testing sampled at a first sampling time for testing to a third sampling time for testing that exists within the first threshold time range from the time when the test subject wakes up and at a fourth sampling time for testing that exists within the second threshold time range from the time when the test subject goes to sleep, respectively, each of the hormone concentration value for learning and the hormone concentration value for testing is calculated.

The hormone concentration value for learning and the hormone concentration value for testing are respectively calculated by analyzing each of the first saliva for learning to the fourth saliva for learning and the first saliva for testing to the fourth saliva for testing through a radioimmunoassay.

The biological data for learning includes a heart rate variability value for learning of the learning subject, and biological data for testing includes a heart rate variability value for testing of the test subject, and in the process (1), after the 1_2th estimated mental health data for learning or the 1_2th GT mental health data, and the biological data for learning including the heart rate variability value for learning of the learning subject are input to the 1_3th estimated model, by referring to the 1_3th estimated mental health data for learning output from the 1_3th estimated model and the 1_3th GT mental health data, the 1_3th estimated model is learned.

The biological data for learning includes brain image data for learning and microbiome data for learning of the learning subject, and the biological data for testing includes brain image data for testing and microbiome data for testing of the test subject, and in the process (1), after the 1_2th estimated mental health data for learning or the 1_2th GT mental health data, and the biological data for learning including the brain image data for learning and the microbiome data for learning of the learning subject are input to the 1_3th estimated model, by referring to the 1_3th estimated mental health data for learning output from the 1_3th estimated model and the 1_3th GT mental health data, the 1_3th estimated model is learned.

The 1_1th psychological data for learning includes adult attachment type information for learning, adverse childhood experiences information for learning, and mind understanding ability information for learning of the learning subject, the 1_2th psychological data for learning includes depression scale information for learning and suicide risk information for learning of the learning subject, the 1_1th psychological data for testing includes adult attachment type information for testing, adverse childhood experiences information for testing, and mind understanding ability information for testing of the test subject, the 1_2th psychological data for testing includes depression scale information for testing and suicide risk information for testing of the test subject, and in the process (1), (i) after the 1_1th psychological data for learning including the adult attachment type information for learning, the adverse childhood experiences information for learning, and the mind understanding ability information for learning is input to the 1_1th estimated model, by referring to the 1_1th estimated mental health data for learning output from the 1_1th estimated model and the 1_1th GT mental health data corresponding to the 1_1th estimated mental health data for learning, the 1_1th estimated model is learned, and (ii) after the 1_1th estimated mental health data for learning or the 1_1th GT mental health data, and the 1_2th psychological data for learning including the depression scale information for learning and the suicide risk information for learning are input to the 1_2th estimated model, by referring to the 1_2th estimated mental health data for learning output from the 1_2th estimated model and the 1_2th GT mental health data corresponding to the 1_2th estimated mental health data for learning, the 1_2th estimated model is learned.

At least a part of the 1_1th psychological data for learning and the 1_2th psychological data for learning further includes recovery resilience information for learning of the learning subject, and at least a part of the 1_1th psychological data for testing and the 1_2th psychological data for testing further includes recovery resilience information for testing of the test subject.

In the process (1), (i) after the psychological data for learning and the biological data for learning of the learning subject are input to the first estimated model, by referring to the estimated mental health data for learning output from the first estimated model and the GT mental health data, the first estimated model is learned, and (ii) after the estimated mental health data for learning or the GT mental health data is input to the second estimated model, by referring to (ii-1) post-treatment estimated mental health data for learning of the learning subject whose mental health status has been changed by applying at least a part of the drug treatment process and the psychotherapy process to the learning subject, (ii-2) estimated drug treatment data for learning for the drug treatment process, and (ii-3) estimated psychotherapy data for learning for the psychotherapy process, which are output from the second estimated model, and post-treatment GT mental health data, GT drug treatment data, and GT psychotherapy data corresponding to each of them, in a state in which the second estimated model is learned, the processor acquires the psychological data for testing and the biological data for testing of the test subject from the terminal of the test subject, in the process (2), the processor inputs the psychological data for testing and the biological data for testing to the first estimated model to allow the first estimated model to output the estimated mental health data for testing, and the processor further includes (c) a process of providing, by the second estimated model, a specific solution for mental health that includes estimated drug treatment data for testing and estimated psychotherapy data for testing for a specific psychotherapy process for a specific drug treatment process, which are to be applied to the test subject during the drug treatment process and the psychotherapy process, by inputting the estimated mental health data for testing by the mental health estimating device to the second estimated model.

Advantageous Effects

According to the present disclosure, it is possible to estimate mental health of a test subject by learning biological and psychological data of healthy people and patients based on machine learning.

In addition, according to the present disclosure, it is possible to provide a suitable solution for mental health to a test subject based on estimated mental health data for the test subject.

DESCRIPTION OF DRAWINGS

The accompany drawings, which are included to provide a further understanding of the present disclosure and are incorporated in and constitute a part of this specification illustrate embodiments of the disclosure and together with the description serve to explain the principles of the present disclosure.

MODE FOR DISCLOSURE

For the detailed description of the present disclosure to be described below, reference is made to the accompanying drawings which show by way of illustration a specific embodiment in which the present disclosure may be practiced in order to clarify the objects, technical solutions, and advantages of the present disclosure. These embodiments will be described in detail to sufficiently enable a person skilled in the art to practice the present disclosure.

In addition, throughout the description and claims of the present disclosure, the word "comprise" and variations thereof are not intended to exclude other technical features, additions, components or steps. Other objects, advantages and characteristics of the present disclosure will appear to a person skilled in the art, in part from this description, and in part from practice of the present disclosure. The examples and drawings below are provided by way of illustration and are not intended to limit the present disclosure.

Moreover, the present disclosure covers all possible combinations of embodiments presented herein. It should be understood that the various embodiments of the present disclosure are different, but need not be mutually exclusive. For example, specific shapes, structures, and characteristics described herein may be implemented in another embodiment without departing from the spirit and the scope of the present invention in connection with an embodiment. In addition, it should be understood that a position or an arrangement of individual components in each disclosed exemplary embodiment may be changed without departing from the spirit and the scope of the present invention. Therefore, a detailed description described below should not be construed as being restrictive. In addition, the scope of the present invention is defined only by the accompanying claims and their equivalents if appropriate. Similar reference numerals will be used to describe the same or similar functions throughout the accompanying drawings.

Hereinafter, preferred embodiments of the present disclosure will be described in detail with reference to the accompanying drawings in order to enable a person with ordinary skill in the art to which the present disclosure pertains to easily implement the present disclosure.

Figure 1:
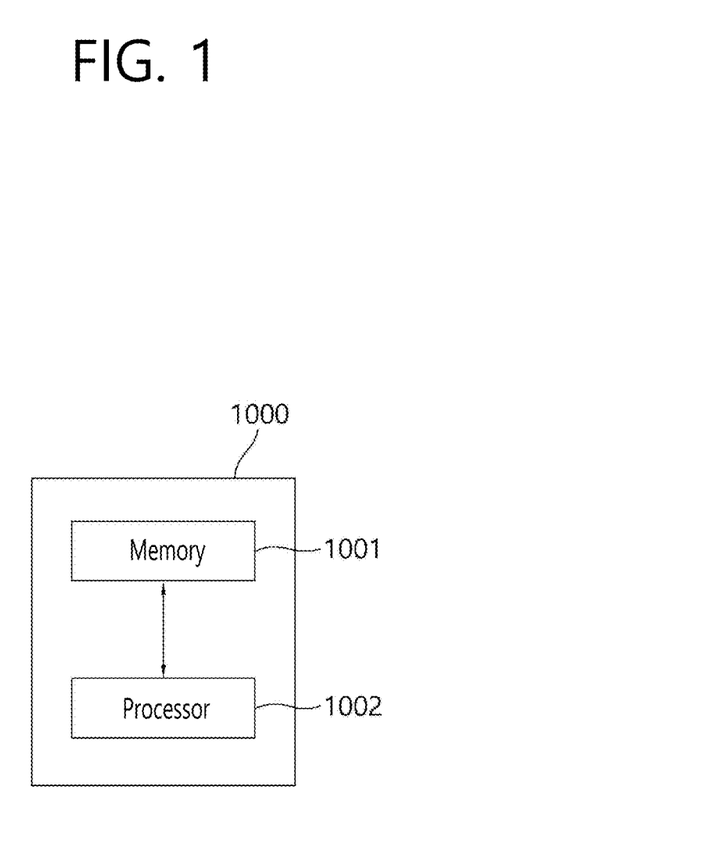
FIG. 1 is a diagram schematically illustrating a mental health estimating device for estimating mental health and providing a solution for mental health by learning psychological data and biological data based on machine learning according to an embodiment of the present disclosure.

FIG. 1 schematically illustrates a mental health estimating device 1000 for estimating mental health and providing a solution for mental health by learning psychological data and biological data based on machine learning according to an embodiment of the present disclosure.

Referring to FIG. 1, the mental health estimating device 1000 may include a memory 1001 that stores instructions for estimating mental health and providing a solution for mental health by learning psychological data and biological data based on machine learning and a processor 1002 that estimates mental health and provides a solution for mental health by learning psychological data and biological data based on machine learning in response to the instructions stored in memory 1001. In this case, the mental health estimating device 1000 may include a personal computer (PC), a mobile computer, a PDA/EDA, a mobile phone, a smart phone, a tablet, an IoT device, and the like. In addition, the mental health estimating device 1000 is not limited thereto, and may include all devices such as a portable game machine having a wired/wireless communication function, a digital camera, and a personal navigation device.

Specifically, the mental health estimating device 1000 typically uses a combination of a computing device (e.g., devices that may include computer processors, memory, storage, input and output devices, and other components of conventional computing devices; electronic communication devices such as routers and switches; electronic information storage systems such as network attached storage (NAS) and storage area networks (SAN)) and computer software (i.e., instructions that cause the computing device to function in a particular way) to achieve desired system performance.

In addition, a processor of the computing device may include a hardware configuration such as a micro processing unit (MPU) or a central processing unit (CPU), a cache memory, and a data bus. In addition, the computing device may further include an operating system and a software configuration of an application for performing a specific purpose.

However, a case in which the computing device includes an integrated processor in which a medium for implementing the present disclosure, a processor, and a memory are integrated is not excluded.

Figure 2:
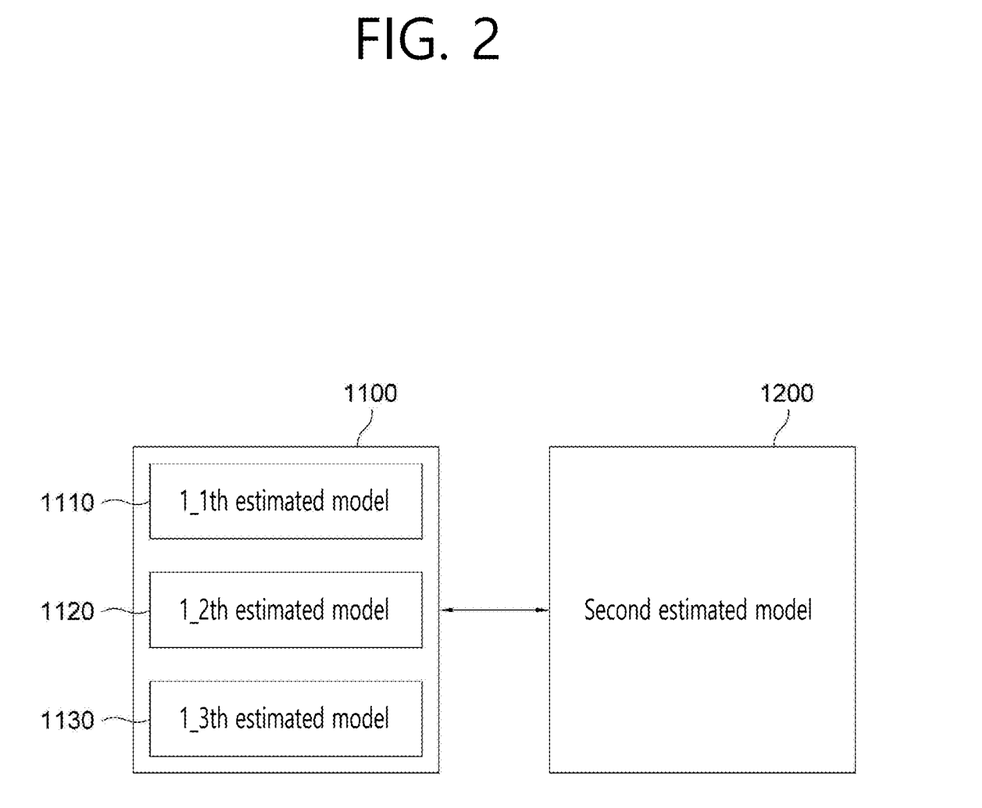
FIG. 2 is a diagram schematically illustrating each estimated model included in the mental health estimating device for estimating mental health and providing a solution for mental health by learning psychological data and biological data based on machine learning according to the embodiment of the present disclosure.

FIG. 2 schematically illustrates each estimated model included in the mental health estimating device 1000 for estimating mental health and providing a solution for mental health by learning psychological data and biological data based on machine learning according to the embodiment of the present disclosure.

Referring to FIG. 2, the mental health estimating device 1000 may include a first estimated model 1100 and a second estimated model 1200, and the first estimated model 1100 may include a 1_1th estimated model 1110, a 1_2th estimated model 1120, and a 1_3th estimated model 1130.

For reference, the 1_1th estimated model 1110, the 1_2th estimated model 1120, the 1_3th estimated model 1130, and the second estimated model 1200 may perform instructions of the mental health estimating device 1000 in the state included in the mental health estimating device 1000, but is not limited thereto.

For example, in a state in which one device (not illustrated) independent of the mental health estimating device 1000 includes all of the 1_1th estimated model 1110, the 1_2th estimated model 1120, the 1_3th estimated model 1130, and the second estimated model 1200, each of the 1_1th estimated model 1110, the 1_2th estimated model 1120, the 1_3th estimated model 1130, and the second estimated model 1200 included in an independent device according to the instructions of the mental health estimating device 1000 may be operated.

Alternatively, in a state in which four devices (not illustrated) independent of the mental health estimating device 1000 each include any one of a 1_1th estimated model 1110, a 1_2th estimated model 1120, a 1_3th estimated model 1130, and a second estimated model 1200, each of the 1_1th estimated model 1110, the 1_2th estimated model 1120, and the 1_3th estimated model included in each independent device according to the instructions of the mental health estimating device 1000 may be operated.

The configuration of the mental health estimating device 1000 for estimating mental health and providing a solution for mental health by learning psychological data and biological data based on machine learning according to the embodiment of the present disclosure is described above.

A method for estimating mental health and providing a solution for mental health by learning psychological data and biological data based on machine learning by the mental health estimating device 1000 configured in this way will be described below.

For reference, in order to avoid confusion in the following description, the phrase "for learning" is added for terms related to the learning process, and the phrase "for testing" is added to terms related to the testing process.

First, the mental health estimating device 1000 may acquire psychological data for testing and biological data for testing of a test subject from a terminal of the test subject in a state in which a first estimated model 1100 is learned by referring to estimated mental health data for learning output from the first estimated model 1100 and ground truth (GT) mental health data corresponding to the estimated mental health data after psychological data for learning and biological data for learning of a plurality of learning subjects are input to the first estimated model 1100.

In addition, the mental health estimating device 1000 may input the psychological data for testing and the biological data for testing to the first estimated model 1100 to allow the first estimated model 1100 to output the estimated mental health data for testing.

In this case, schematically describing the learning of the first estimated model 1100, after the psychological data for learning and the biological data for learning are acquired and input to the first estimated model 1100, by referring to estimated mental health data for learning output from the first estimated model 1100 and GT mental health data corresponding to the estimated mental health data for learning, a loss may be calculated. Further, at least one parameter of the first estimated model 1100 may be learned by performing backpropagation using the loss.

For reference, the estimated mental health data for learning may indicate estimated data of the first estimated model 1100 for a current mental health status of the learning subject, and the GT mental health data may indicate answer data for a current mental health status of the learning subject.

The general flow is the same as above, which will be described below in more detail with reference to FIG. 3.

Figure 3:
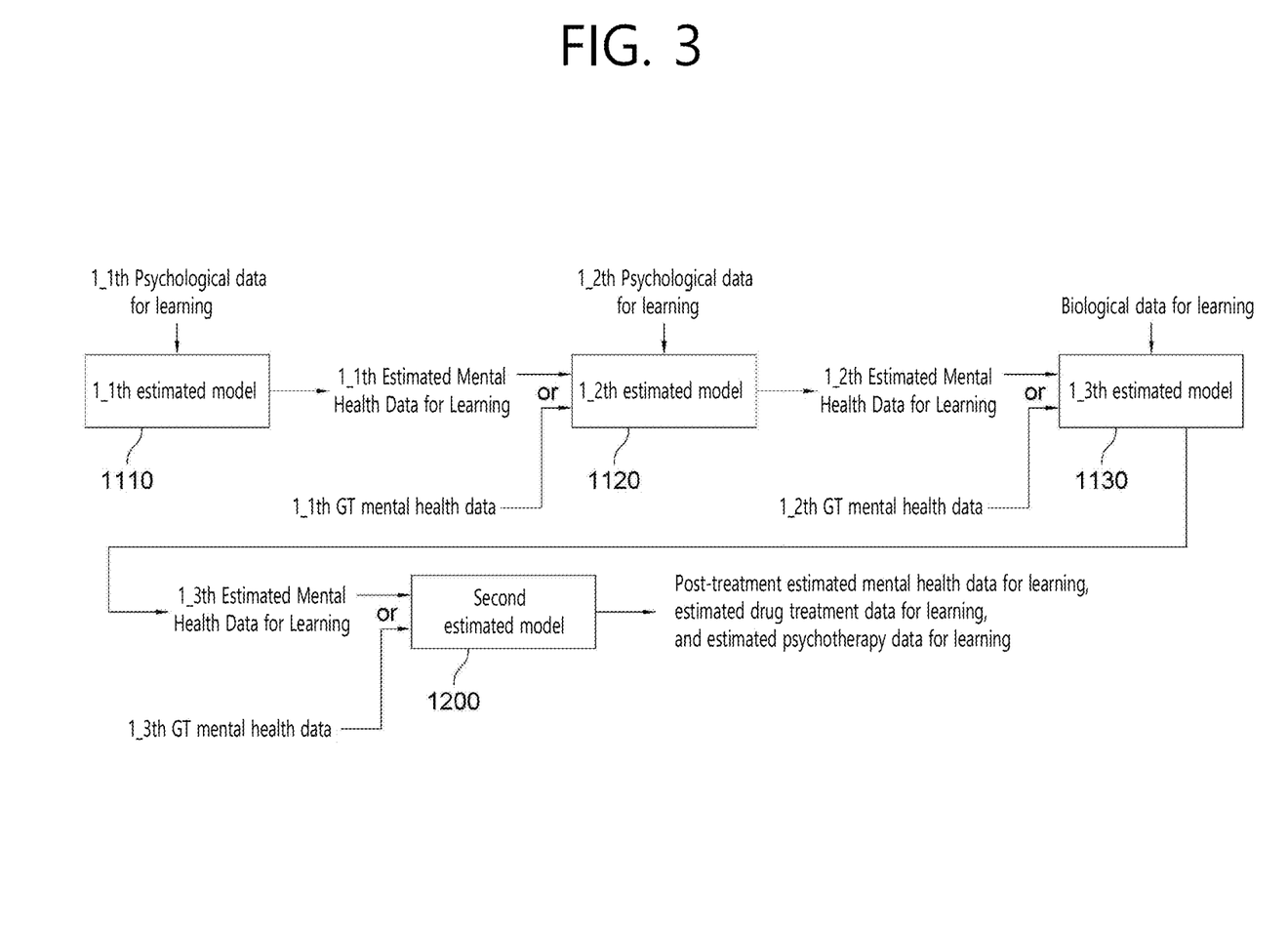
FIG. 3 is a diagram schematically illustrating a learning process of estimating mental health and providing a solution for mental health by learning psychological data and biological data based on machine learning according to an embodiment of the present disclosure.

FIG. 3 schematically illustrates a learning process of estimating mental health and providing a solution for mental health by learning psychological data and biological data based on machine learning according to an embodiment of the present disclosure.

Referring to FIG. 3, describing the learning process of extracting mental health and providing a solution for mental health by learning psychological data and biological data based on machine learning, first, after 1_1th psychological data for learning including at least a part of a 1_1th positive psychological information for learning and a 1_1th negative psychological information for learning of a learning subject is input to a 1_1th estimated model 1110, by referring to 1_1th estimated mental health data for learning output from the 1_1th estimated model 1110 and 1_1th GT mental health data corresponding to the 1_1th estimated mental health data for learning, the 1_1th estimated model 1110 may be learned.

In this case, the 1_1th psychological data for learning may include adult attachment type information for learning, adverse childhood experiences information for learning, and mind understanding ability information for learning of the learning subject. In addition, the 1_1th psychological data for learning may further include recovery resilience information for learning of the learning subject.

Describing in detail each information included in the 1_1th psychological data for learning, the adult attachment type information for learning may indicate type information classified into any one of four types of a secure type, an anxious type, an avoidant type, and a disorganized type according to scores on two axes corresponding to an anxiety score and an avoidance score.

For example, when the anxiety score of the learning subject is high and the avoidance score is low, the adult attachment type information for learning may indicate the type information classified into the anxious type, and when both the anxiety and avoidance scores of the learning subject are high, the adult attachment type information for learning may indicate the type information classified into the confused type.

In addition, adverse childhood experiences information for learning may include six sub-factors of emotional abuse, biological abuse, sexual abuse, neglect, exposure to domestic violence, and bullying, and may indicate the scores of the learning subject calculated based on scores according to each sub-factor.

In addition, the mind understanding ability information for learning may include five sub-factors of lack of recognition of emotions, lack of emotional expression and interaction, mind and reality identification, hasty mind understanding, and lack of understanding other people's minds, and may indicate the scores of the learning subject calculated based on scores according to each sub-factor.

Specifically, (i) the factor of lack of recognition of emotion is a sub-factor indicating whether it is difficult to understand the learning subject's own emotions in detail and clearly, (ii) the factor of lack of emotional expression and interaction is a sub-factor indicating whether the learning subject's attitude to expressing or interacting with others is insufficient, (iii) the factor of mental and reality identification is a sub-factor indicating whether the learning subject has the rigidity to perceive that what he or she thinks and feels is the same as the actual reality, (iv) the factor of considering hasty mind is a sub-factor indicating whether there is a tendency to intuitively and hastily determine other people's thoughts or emotions, and (v) the factor of lack in understanding other people's minds is a sub-factor indicating whether a motivation to think about other people's minds is insufficient.

In addition, the recovery resilience information for learning may include three sub-factors of self-regulation ability, interpersonal ability, and positivity, and may indicate scores of the learning subject calculated based on scores according to each sub-factor.

Meanwhile, 1_1th positive psychological information for learning of a learning subject may include mind understanding ability information for learning and recovery resilience information for learning of a learning subject, and 1_1th negative psychological information for learning may include adult attachment type information for learning and adverse childhood experiences information for learning.

To help understanding, a specific example for the process in which the 1_1th estimated mental health data for learning is output by the 1_1th estimated model 1110 will be described.

As an example, (i) the 1_1th adult attachment type information for learning of the learning subject included in the psychological data for learning may indicate the type information of the "secure type" which is a result classified based on scores on two axes, (ii) the adverse childhood experiences information for learning may indicate "0 points" which is a result calculated based on the scores according to the six sub-factors, and (iii) the mind understanding ability information of the learning subject may indicate "high" which is a result calculated based on the scores according to the five sub-factors.

In this case, the 1_1th GT mental health data may be data indicating "good" among three of "good," "normal,", and "caution." On the other hand, the 1_1th estimated model 1110 may output the 1_1th estimated mental health data for learning that indicates "normal" rather than "good" for the 1_1th psychological data for learning as described above.

Then, by referring to the 1_1th GT mental health data indicating "good" and the 1_1th estimated mental health data for learning indicating "normal," the loss may be calculated, and by backpropagating the loss, at least one parameter of the 1_1th estimated model 1110 may be learned.

By repeating this process, the 1_1th estimated model 1110 may output the 1_1th estimated mental health data for learning which indicates "good" which is a correct answer value for the 1_1th psychological data for learning as described above.

Meanwhile, the description of the learning process is similarly applied to the 1_2th estimated model 1120, the 1_3th estimated model 1130, and the second estimated model 1200, and therefore, the overlapping description will be omitted.

After (i) 1_1th estimated mental health data for learning or 1_1th GT mental health data and (ii) 1_2th psychological data for learning including at least a part of the 1_2th positive psychological information for learning and the 1_2th negative psychological information for learning of the learning subject are input to the 1_2th estimated model 1120, by referring to the 1_2th estimated mental health data for learning output from the 1_2th estimated model 1120 and the 1_2th GT mental health data corresponding to the 1_2th estimated mental health data for learning, the 1_2th estimated model 1120 may be learned.

In this case, the 1_2th psychological data for learning may include depression scale information for learning and suicide risk information for learning of the learning subject. In addition, the 1_2th psychological data for learning may further include recovery resilience information for learning of the learning subject.

Describing in detail each piece of information included in the 1_2th psychological data for learning, the depression scale information for learning may indicate the depression symptom assessment result information of five stages of no depression, mild, moderate, severe, and highest.

In addition, the suicide risk information for learning may indicate suicide risk assessment result information of three stages of low, boundary, and high.

To help understanding, a specific example for the process in which the 1_2th estimated mental health data for learning is output by the 1_2th estimated model 1120 will be described.

For example, when (i) the 1_1th estimated mental health data for learning indicates "good," (ii) the depression scale information for learning of the learning subject included in the 1_2th psychological data for learning indicates depression symptom assessment result information corresponding to the "no depression" stage, (iii) the suicide risk information for learning of the learning subject included in the 1_2th psychological data for learning indicates the suicide risk assessment result information corresponding to the 'low' stage, the 1_2th estimated model 1120 may output the 1_2th estimated mental health data for learning corresponding to the "normal" stage among the four stages of "normal," "attention," "boundary," and "risky."

As another example, when (i) the 1_1th GT mental health data indicates "normal," (ii) the depression scale information for learning of the learning subject included in the 1_2th psychological data for learning indicates the depression symptom assessment result information corresponding to the "hard" stage, and (iii) the suicide risk information for learning of the learning subject included in the 1_2th psychological data for learning indicates suicide risk assessment result information corresponding to the "boundary" stage, the 1_2th estimated model 1120 may output the 1_2th estimated mental health data for learning corresponding to "attention" among the four "normal," "attention," "boundary," and "risky."

After (i) the 1_2th estimated mental health data for learning or the 1_2th GT mental health data, and (ii) the biological data for learning is input to the 1_3th estimated model 1130, by referring to the 1_3th estimated mental health data for learning output from the 1_3th estimated model 1130 and the 1_3th GT mental health data corresponding to the 1_3th estimated mental health data for learning, the 1_3th estimated model 1130 may be learned.

As an example, the biological data for learning may include a hormone concentration value for learning of a learning subject.

As another example, the biological data for learning may include a heart rate variability value for learning of a learning subject.

As another example, the biological data for learning may include brain image data for learning and microbiome data for learning of a learning subject.

Hereinafter, the process of learning the 1_3th estimated model 1130 by using the biological data for learning including a hormone concentration value for learning will be representatively described, and the above description is similarly applied to the process in which the 1_3th estimated model 1130 is learned by using the biological data for learning including at least a part of the heart rate variability value for learning, the brain image data for learning, and the microbiome data for learning, and therefore, the overlapping description thereof will be omitted.

Specifically, after (i) the 1_2th estimated mental health data for learning or the 1_2th GT mental health data, and (ii) the biological data for learning including the hormone concentration value for learning of the learning subject is input to the 1_3th estimated model 1130, by referring to the 1_3th estimated mental health data for learning output from the 1_3th estimated model 1130 and the 1_3th GT mental health data, the 1_3th estimated model 1130 may be learned.

In this case, by analyzing first saliva for learning to fourth saliva for learning sampled at (i) first sampling time for learning to a third sampling time for learning existing within a first threshold time range from a time when the learning subject wakes up, and (ii) a fourth sampling time for learning within a second threshold time range from a time when the learning subject goes to sleep, a hormone concentration value for learning may be calculated.

For example, when a first threshold time range is set to 90 minutes, the second threshold time range is set to 60 minutes, a time when a learning subject wakes up is 7:00 am, and a time when the learning subject goes to sleep is 10:00 pm, the first sampling time for learning may be 7:00 am immediately after waking up, the second sampling time for learning may be 7:30 am, the third sampling time for learning may be 8:00 am, and the fourth sampling time for learning may be 9:00 pm the night before.

In addition, the hormone concentration value for learning may be calculated by analyzing the first saliva for learning to the fourth saliva for learning sampled as above by radioimmunoassay.

As such, when using the radioimmunoassay, it is possible to measure even a very trace amount of hormone, so the radioimmunoassay has the advantage that the measurement sensitivity is much higher than that of enzyme immunoassay (EIA).

In addition, the mental health estimating device 1000 may provide an alarm to the learning subject at every first sampling time for learning to fourth sampling time for learning to sample the saliva for learning from the learning subject at the correct sampling time, thereby increasing the reliability of the hormone analysis results.

Meanwhile, the hormone concentration value for learning may include a Cortisol concentration value for learning and a dehydroepiandrosterone (DHEA) concentration value for learning. In addition, the hormone concentration value for learning may additionally include a sex hormone concentration value for learning.

In this case, when the sex hormone concentration value for learning meets a threshold range, in a state in which a first weight applied to the 1_1th positive psychological information for learning and the 1_2th positive psychological information for learning is set to be smaller than a second weight applied to the 1_1th negative psychological information for learning and the 1_2th negative psychological information for learning, the 1_1th estimated model 1110 to the 1_3th estimated model 1130 may be learned.

For example, when gender information (female) of a learning subject is obtained and a concentration value of progesterone, which is a sex hormone, meets the first threshold range, in a state in which the mental health estimating device 1000 sets a first weight, which is applied to the mind understanding ability information for learning and the recovery resilience information for learning, to be smaller than 1, and set a second weight, which is applied to the adverse childhood experiences information for learning, to be greater than 1, the 1_1th estimated model 1110 to the 1_3th estimated model 1130 may be learned.

For example, when gender information (male) of the learning subject is obtained and a concentration value of testosterone, which is a sex hormone, meets a first threshold range, in a state in which the mental health estimating device 1000 sets the first weight, which is applied to the mind understanding ability information for learning and the recovery resilience information for learning, to be smaller than 1 and sets the second weight, which is applied to the adverse childhood experiences information for learning, to be greater than 1, the information indicating that the learning subject has entered puberty may be output.

As another example, when the gender information (male) of the learning subject is obtained and the concentration value of testosterone, which is a sex hormone, satisfies a third threshold range, in a state in which the mental health estimating device 1000 sets a first weight, which is applied to the mind understanding ability information for learning and the recovery resilience information for learning, to be smaller than 1 and sets a second weight, which is applied to the adverse childhood experiences information for learning, to be greater than 1, the 1_1th estimated model 1110 to the 1_3th estimated model 1130 may be learned, and the information indicating that the learning subject has currently entered male menopause may be output.

So far, the learning process of the first estimated model 1100 that includes the 1_1th estimated model 1110, the 1_2th estimated model 1120, and the 1_3th estimated model 1130, has been described, and the learning process of the second estimated model 1200 will be described below.

As described above, after the psychological data for learning and the biological data for learning for the learning subject are acquired and input to the first estimated model 1100, by referring to the estimated mental health data for learning output from the first estimated model 1100 and the GT mental health data, the first estimated model 1100 may be learned, and the estimated mental health data for learning from the first estimated model 1100 or the GT mental health data corresponding to the estimated mental health data for learning may be input to the second estimated model 1200.

Referring to FIG. 3, it may be confirmed that (i) the 1_3th estimated mental health data for learning output from 1_3th estimated model 1130 is input to the second estimated model 1200 as the estimated mental health data for learning, or (ii) the 1_3th GT mental health data is input to the second estimated model 1200 as the GT mental health data.

In addition, by referring to (i) post-treatment estimated mental health data for learning for a learning subject whose mental health status has been changed by applying at least a part of the drug treatment process and psychotherapy process output from the second estimated model 1200 to the learning subject, (ii) estimated drug treatment data for learning for the drug treatment process, (iii) estimated psychotherapy data for learning for the psychotherapy process, (iv) post-treatment GT mental health data, (v) GT drug treatment data, and (vi) GT psychotherapy data, the second estimated model 1200 may be learned.

In this case, (i) the estimated mental health data for learning may indicate the estimated result of the first estimated model 1100 for the current mental health status of the learning subject, (ii) the GT mental health data may indicate the current mental health status of the learning subject, (iii) the post-treatment estimated mental health data for learning may indicate the estimated result of the second estimated model 1200 for mental health status after the treatment of a learning subject whose mental health status has been changed by applying at least a part of the drug treatment process and the psychotherapy process to the learning subject results, (v) the estimated drug treatment data for learning may indicate the estimated results of the second estimated model 1200 for the drug treatment process applied to the learning subject, (vi) the GT drug treatment data may include information on the actual drug treatment process applied to the learning subject, (vii) the estimated psychotherapy data for learning may indicate the estimated results of the second estimated model 1200 for the psychotherapy process applied to the learning subject, and (viii) the GT psychotherapy data may include information on the actual psychotherapy process applied to the learning subject.

As such, in the state where the 1_1th estimated model 1110 to 1_3th estimated model 1130 and the second estimated model 1200 are learned, the description of the test process of estimating mental health and providing a solution for mental health is as follows.

For reference, the description of the learning data and the learning information is similarly applied to the description of the test data and the test information, and therefore, the overlapping description will be omitted for convenience of description.

First, the mental health estimating device 1000 may acquire the psychological data for testing and the biological data for testing of the test subject from the terminal of the test subject.

In addition, the mental health estimating device inputs psychological data for testing and biological data for testing to the first estimated model 1100 to allow the first estimated model 1100 to output the estimated mental health data for testing.

In addition, the mental health estimating device may input the estimated mental health data for testing to the second estimated model 1200 to provide the second estimated model 1200 to provide a specific solution for mental health that includes estimated drug treatment data for testing for a specific drug treatment process and estimated psychotherapy data for testing for a specific psychotherapy process which are to be applied to the test subject during the drug treatment process and the psychotherapy process.

The general flow is the same as above, which will be described below in more detail with reference to FIG. 4.

Figure 4:
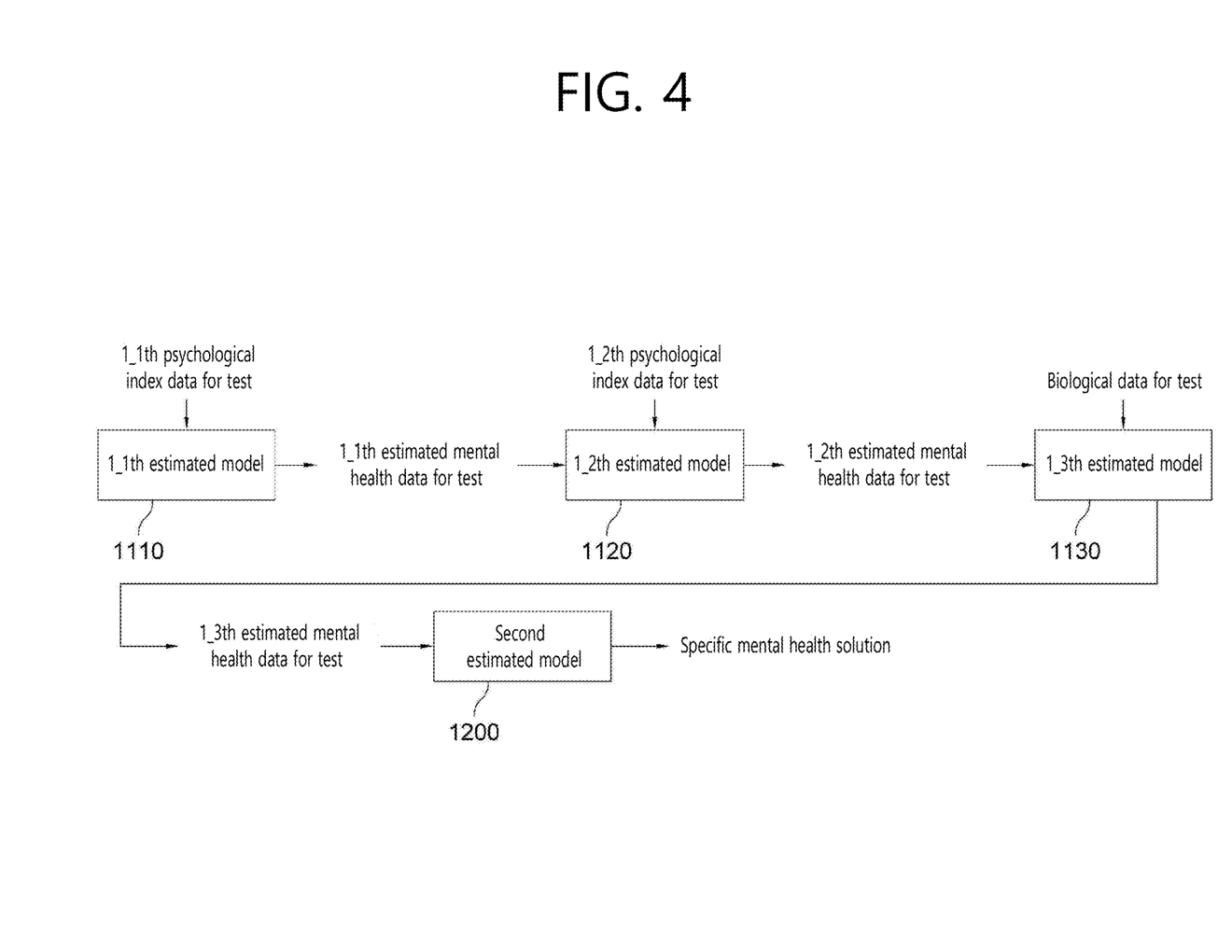
FIG. 4 is a diagram schematically illustrating a test process of estimating mental health and providing a solution for mental health by learning psychological data and biological data based on machine learning according to an embodiment of the present disclosure.

FIG. 4 schematically illustrates a test process of estimating mental health and providing a solution for mental health by learning psychological data and biological data based on machine learning according to an embodiment of the present disclosure.

First, the mental health estimating device 1000 may acquire the 1_1th psychological data for testing, the 1_2th psychological data for testing, and the biological data for testing of the test subject from the terminal of the test subject.

In addition, the mental health estimating device 1000 inputs the 1_1th psychological data for testing to the 1_1th estimated model 1110 to allow the 1_1th estimated model 1110 to output the 1_1th estimated mental health data for testing. In addition, the mental health estimating device 1000 may input the 1_1th estimated mental health data for testing and the 1_2th psychological data for testing to the 1_2th estimated model 1120 to allow the 1_2th estimated model 1120 to output the 1_2th estimated mental health data for testing. In addition, the mental health estimating device 1000 may input the 1_2th estimated mental health data for testing and the biological data for testing to the 1_3th estimated model 1130 to allow the 1_3th estimated model 1130 to output the 1_3th estimated mental health data for testing.

That is, the mental health estimating device 1000 may allow the first estimated model 1100 including the 1_1th estimated model 1110 to the 1_3th estimated model 1130 to output the estimated mental health data for testing which is an estimated value indicating the current mental health status of the test subject.

By referring to the output estimated mental health data for testing, (i) the kind of mental disease the test subject currently has, (ii) the severity of the test subject with a specific mental disease, and the like may be identified.

In addition, the mental health estimating device 1000 may input the 1_3th estimated mental health data for testing to the second estimated model 1200 to provide the second estimated model 1200 to provide a specific solution for mental health that includes estimated drug treatment data for testing for a specific drug treatment process and estimated psychotherapy data for testing for a specific psychotherapy process which are to be applied to the test subject during the drug treatment process and the psychotherapy process.

For example, the specific estimated mental health data for testing may be data indicating that a specific test subject currently suffers from severe depression. In such a case, the second estimated model 1200 may refer to specific estimated mental health data for testing to provide a specific solution for mental health including information on the need for specific medication and specific psychotherapy for a specific test subject.

Figure 5:
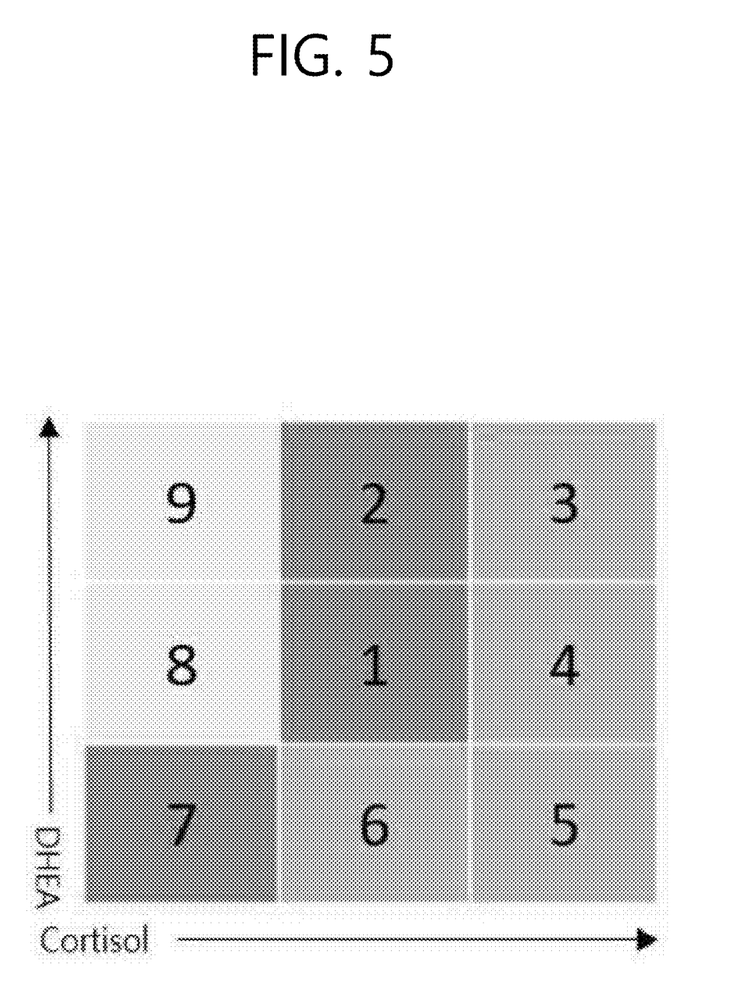
FIG. 5 is a diagram schematically illustrating some information included in estimated mental health data for testing for estimating mental health and providing a solution for mental health by learning psychological data and biological data based on machine learning according to the embodiment of the present disclosure.

Meanwhile, FIG. 5 schematically illustrates some information included in estimated mental health data for testing that is provided by the mental health estimating device 1000 for estimating mental health and providing a solution for mental health by learning psychological data and biological data based on machine learning according to the embodiment of the present disclosure.

As an example, the estimated mental health data for testing may include information about the Cortisol concentration value and the DHEA concentration value calculated by analyzing the first saliva for testing to the fourth test saliva collected from the test subject.

Describing with reference to FIG. 5, (i) a region corresponding to grid No. 1 indicates that an adrenal function of a test subject is in a normal state, (ii) a region corresponding to grid No. 2 indicates that the adrenal function of the test subject is in a normal state, but when the high DHEA level persists, it indicates that a medical check is required, (iii) a region corresponding to grid No. 3 indicates the state in which the adrenal function of the test subject responds to acute stress, (iv) a region corresponding to grid No. 4 indicates the state of the adrenal function of the test subject tolerating continuous acute stress, (v) a region corresponding to grid No. 5 indicates the state in which the adrenal function of the test subject are primarily resistant to continuous stress, (vi) a region corresponding to grid No. 6 indicates the state in which the test subject's adrenal functions are secondary to the continuous stress, (vii) a region corresponding to grid No. 7 indicates the state in which the adrenal function of the test subject is exhausted due to chronic stress, and (viii) regions corresponding to grid Nos. 8 and 9 indicate that the adrenal function of the test subject is not in a natural state.

For example, when the region corresponding to the cortisol concentration value and the DHEA concentration value calculated by analyzing the first saliva for testing to the fourth test saliva sampled from the test subject is region No. 9, the Cortisol concentration of the test subject is higher than the normal level, since the DHEA appears to be in the normal range or higher than the normal range in the low state, the mental health estimating device 1000 may output the estimated mental health data for testing that includes information on the effect that a comprehensive review is necessary because these results occurred due to biological diseases or artificially taken drugs, or saliva sampling was not performed accurately, and the graph shown in FIG. 5.

In addition, embodiments according to the present disclosure described above may be implemented in a form of program instructions that may be executed through various computer components and may be recorded in a computer-readable recording medium. The computer-readable recording medium may include a program command, a data file, a data structure, or the like, alone or a combination thereof. The program instructions recorded in the computer-readable recording medium may be especially designed and constituted for the present disclosure or be known to those skilled in the field of computer software. Examples of the computer-readable recording media may include a magnetic medium such as a hard disk, a floppy disk, or a magnetic tape, an optical recording medium such as a compact disk read only memory (CD-ROM) or a digital versatile disk (DVD), a magneto-optical medium such as a floptical disk, and a hardware device specially configured to store and execute program commands, such as a read only memory (ROM), a random access memory (RAM), a flash memory, or the like. Examples of the program instructions include a high-level language code capable of being executed by a computer using an interpreter, or the like, as well as a machine language code created by a compiler. The hardware device may be constituted to be operated as one or more software modules to perform processing according to the present disclosure, and vice versa.

Hereinabove, although the present disclosure has been described by specific matters such as detailed components, exemplary embodiments, and the accompanying drawings, they have been provided only for assisting in the entire understanding of the present disclosure. Therefore, the present disclosure is not limited to the exemplary embodiments. Various modifications and changes may be made by those skilled in the art to which the present disclosure pertains from this description.

Therefore, the spirit of the present disclosure should not be limited to these exemplary embodiments, but the claims and all of modifications equal or equivalent to the claims are intended to fall within the scope and spirit of the present disclosure.

The invention claimed is:

1. A method for estimating mental health and providing a solution for mental health by learning psychological data and biological data based on machine learning, the method comprising:
   (a) acquiring, by a mental health estimating device, psychological data for testing and biological data for testing of a test subject from a terminal of the test subject in a state in which a first estimated model is learned by referring to estimated mental health data for learning output from the first estimated model and ground truth (GT) mental health data corresponding to the estimated mental health data, after psychological data for learning and biological data for learning of a plurality of learning subjects are input to the first estimated model;
   (b) inputting, by the mental health estimating device, the psychological data for testing and the biological data for testing to the first estimated model to allow the first estimated model to output estimated mental health data for testing; and
   (c) providing, by a second estimated model, a specific solution for mental health that includes estimated drug treatment data for testing and estimated psychotherapy data for testing for a specific psychotherapy process for a specific drug treatment process, which are to be applied to the test subject during the drug treatment process and the psychotherapy process, by inputting the estimated mental health data for testing by the mental health estimating device to the second estimated model.

2. The method of claim 1, wherein the first estimated model includes a 1_1th estimated model, a 1_2th estimated model and a 1_3th estimated model, in the step (a),
   (i) after 1_1th psychological data for learning including at least a part of 1_1th positive psychological information for learning and 1_1th negative psychological information for learning of the learning subject is input to the 1_1th estimated model, by referring to 1_1th estimated mental health data for learning output from the 1_1th estimated model and 1_1th GT mental health data corresponding to the 1_1th estimated mental health data, the 1_1th estimated model is learned, (ii) after the 1_1th estimated mental health data for learning or the 1_1th GT mental health data, and 1_2th learning psychological data including at least a part of 1_2th positive psychological information for learning and 1_2th negative psychological information for learning of the learning subject is input to the 1_2th estimated model, by referring to the 1_2th estimated mental health data for learning output from the 1_2th estimated model and 1_2th GT mental health data corresponding to the 1_2th estimated mental health data for learning, the 1_2th estimated model is learned, and (iii) after the 1_2th estimated mental health data for learning or the 1_2th GT mental health data, and the biological data for learning are input to the 1_3th estimated model, by referring to the 1_3th estimated mental health data for learning output from the 1_3th estimated model and 1_3th GT mental health data corresponding to the 1_3th estimated mental health data for learning, in a state in which the 1_3th estimated model is learned, the mental health estimating device acquires 1_1th psychological data for testing, 1_2th psychological data for testing, and the biological data for testing of the test subject from the terminal of the test subject, and
   in the step (b),
   the mental health estimating device (i) inputs the 1_1th psychological data for testing to the 1_1th estimated model to allow the 1_1th estimated model to output 1_1th estimated mental health data for testing, (ii) inputs the 1_1th estimated mental health data for testing and the 1_2th psychological data for testing to the 1_2th estimated model to allow the 1_2th estimated model to output 1_2th estimated mental health data for testing, and (iii) inputs the 1_2th estimated mental health data for testing and the biological data for testing to the 1_3th estimated model to allow the 1_3th estimated model to output 1_3th estimated mental health data for testing.

3. The method of claim 2, wherein the biological data for learning includes a hormone concentration value for learning of the learning subject, and the biological data for testing includes a hormone concentration value for testing of the test subject, and
   in the step (a),
   after the 1_2th estimated mental health data for learning or the 1_2th GT mental health data, and the biological data for learning including the hormone concentration value for learning of the learning subject are input to the 1_3th estimated model, by referring to the 1_3th estimated mental health data for learning output from the 1_3th estimated model and the 1_3th GT mental health data, the 1_3th estimated model is learned.

4. The method of claim 3, wherein the hormone concentration value for learning includes a Cortisol concentration value for learning and a dehydroepiandrosterone (DHEA) concentration value for learning, and the hormone concentration value for testing includes a Cortisol concentration value for testing and a DHEA concentration value for testing.

5. The method of claim 4, wherein the hormone concentration value for learning further includes a sex hormone concentration value for learning, and the hormone concentration value for testing further includes a sex hormone concentration value for testing, and
   in the step (a),
   when the sex hormone concentration value for learning meets a threshold range, in a state in which a first weight applied to the 1_1th positive psychological information for learning and the 1_2th positive psychological information for learning is set to be smaller than a second weight applied to the 1_1th negative psychological information for learning and the 1_2th negative psychological information for learning, the 1_1th estimated model to the 1_3th estimated model are learned.

6. The method of claim 3, wherein, by analyzing (i) first saliva for learning to fourth saliva for learning sampled at a first sampling time for learning to a third sampling time for learning that exists within a first threshold time range from a time when the learning subject wakes up, and at a fourth sampling time for learning that exists within a second threshold time range from a time when the learning subject goes to sleep, and (ii) first saliva for testing to fourth saliva for testing sampled at a first sampling time for testing to a third sampling time for testing that exists within the first threshold time range from the time when the test subject wakes up and at a fourth sampling time for testing that exists within the second threshold time range from the time when the test subject goes to sleep, respectively, each of the hormone concentration value for learning and the hormone concentration value for testing is calculated.

7. The method of claim 6, wherein the hormone concentration value for learning and the hormone concentration value for testing are respectively calculated by analyzing each of the first saliva for learning to the fourth saliva for learning and the first saliva for testing to the fourth saliva for testing through a radioimmunoassay.

8. The method of claim 2, wherein the biological data for learning includes a heart rate variability value for learning of the learning subject, and the biological data for testing includes a heart rate variability value for testing of the test subject, and
in the step (a),
after the 1_2th estimated mental health data for learning or the 1_2th GT mental health data, and the biological data for learning including the heart rate variability value for learning of the learning subject are input to the 1_3th estimated model, by referring to the 1_3th estimated mental health data for learning output from the 1_3th estimated model and the 1_3th GT mental health data, the 1_3th estimated model is learned.

9. The method of claim 2, wherein the biological data for learning includes brain image data for learning and microbiome data for learning of the learning subject, and the biological data for testing includes brain image data for testing and microbiome data for testing of the test subject, and
in the step (a),
after the 1_2th estimated mental health data for learning or the 1_2th GT mental health data, and the biological data for learning including the brain image data for learning and the microbiome data for learning of the learning subject are input to the 1_3th estimated model, by referring to the 1_3th estimated mental health data for learning output from the 1_3th estimated model and the 1_3th GT mental health data, the 1_3th estimated model is learned.

10. The method of claim 2, wherein the 1_1th psychological data for learning includes adult attachment type information for learning, adverse childhood experiences information for learning, and mind understanding ability information for learning of the learning subject,
the 1_2th psychological data for learning includes depression scale information for learning and suicide risk information for learning of the learning subject,
the 1_1th psychological data for testing includes adult attachment type information for testing, adverse childhood experiences information for testing, and mind understanding ability information for testing of the test subject,
the 1_2th psychological data for testing includes depression scale information for testing and suicide risk information for testing of the test subject, and
in the step (a),
(i) after the 1_1th psychological data for learning including the adult attachment type information for learning, the adverse childhood experiences information for learning, and the mind understanding ability information for learning is input to the 1_1th estimated model, by referring to the 1_1th estimated mental health data for learning output from the 1_1th estimated model and the 1_1th GT mental health data corresponding to the 1_1th estimated mental health data for learning, the 1_1th estimated model is learned, and (ii) after the 1_1th estimated mental health data for learning or the 1_1th GT mental health data, and the 1_2th psychological data for learning including the depression scale information for learning and the suicide risk information for learning are input to the 1_2th estimated model, by referring to the 1_2th estimated mental health data for learning output from the 1_2th estimated model and the 1_2th GT mental health data corresponding to the 1_2th estimated mental health data for learning, the 1_2th estimated model is learned.

11. The method of claim 10, wherein at least a part of the 1_1th psychological data for learning and the 1_2th psychological data for learning further includes recovery resilience information for learning of the learning subject, and
at least a part of the 1_1th psychological data for testing and the 1_2th psychological data for testing further includes recovery resilience information for testing of the test subject.

12. The method of claim 1, wherein in the step (a),
(i) after the psychological data for learning and the biological data for learning of the learning subject are input to the first estimated model, by referring to the estimated mental health data for learning output from the first estimated model and the GT mental health data, the first estimated model is learned, and (ii) after an estimated mental health data for learning or the GT mental health data is input to a second estimated model, by referring to (ii-1) post-treatment estimated mental health data for learning of the learning subject whose mental health status has been changed by applying at least a part of a drug treatment process and a psychotherapy process to the learning subject, (ii-2) estimated drug treatment data for learning for the drug treatment process, and (ii-3) estimated psychotherapy data for learning for the psychotherapy process, which are output from the second estimated model, and post-treatment GT mental health data, GT drug treatment data, and GT psychotherapy data corresponding to each of them, in a state in which the second estimated model is learned, the mental health estimating device acquires the psychological data for testing and the biological data for testing of the test subject from the terminal of the test subject, and
in the step (b),
the mental health estimating device inputs the psychological data for testing and the biological data for testing to the first estimated model to allow the first estimated model to output the estimated mental health data for testing.

13. A mental health estimating device for estimating mental health and providing a solution for mental health by learning psychological data and biological data based on machine learning, the mental health estimating device comprising:

at least one memory configured to store instructions; and
at least one processor configured to execute the instructions,
wherein the processor (1) performs a process of acquiring psychological data for testing and biological data for testing of a test subject from a terminal of the test subject in a state in which a first estimated model is learned by referring to estimated mental health data for learning output from the first estimated model and ground truth mental health data corresponding to the estimated mental health data for learning after psychological data for learning and biological data for learning of a plurality of learning subjects are input to the first estimated model, (2) performs a process of inputting the psychological data for testing and the biological data for testing to the first estimated model to allow the first estimated model to output estimated mental health data for testing, and (3) provides, by a second estimated model, a specific solution for mental health that includes estimated drug treatment data for testing and estimated psychotherapy data for testing for a specific psychotherapy process for a specific drug treatment process, which are to be applied to the test subject during the drug treatment process and the psychotherapy process, by inputting the estimated mental health data for testing by the mental health estimating device to the second estimated model.

14. The mental health estimating device of claim 13, wherein the first estimated model includes a 1_1th estimated model, a 1_2th estimated model and a 1_3th estimated model, and in the process (1),
(i) after 1_1th psychological data for learning including at least a part of 1_1th positive psychological information for learning and 1_1th negative psychological information for learning of the learning subject is input to the 1_1th estimated model, by referring to 1_1th estimated mental health data for learning output from the 1_1th estimated model and 1_1th GT mental health data corresponding to the 1_1th estimated mental health data, the 1_1th estimated model is learned, (ii) after the 1_1th estimated mental health data for learning or the 1_1th GT mental health data, and 1_2th learning psychological data including at least a part of 1_2th positive psychological information for learning and 1_2th negative psychological information for learning of the learning subject is input to the 1_2th estimated model, by referring to the 1_2th estimated mental health data for learning output from the 1_2th estimated model and 1_2th GT mental health data corresponding to the 1_2th estimated mental health data for learning, the 1_2th estimated model is learned, and (iii) after the 1_2th estimated mental health data for learning or the 1_2th GT mental health data, and the biological data for learning are input to the 1_3th estimated model, by referring to the 1_3th estimated mental health data for learning output from the 1_3th estimated model and 1_3th GT mental health data corresponding to the 1_3th estimated mental health data for learning, in a state in which the 1_3th estimated model is learned, the processor acquires 1_1th psychological data for testing, 1_2th psychological data for testing, and the biological data for testing of the test subject from the terminal of the test subject, and in the process (2),
the processor (i) inputs the 1_1th psychological data for testing to the 1_1th estimated model to allow the 1_1th estimated model to output 1_1th estimated mental health data for testing, (ii) inputs the 1_1th estimated mental health data for testing and the 1_2th psychological data for testing to the 1_2th estimated model to allow the 1_2th estimated model to output 1_2th estimated mental health data for testing, and (iii) inputs the 1_2th estimated mental health data for testing and the biological data for testing to the 1_3th estimated model to allow the 1_3th estimated model to output 1_3th estimated mental health data for testing.

15. The mental health estimating device of claim 14, wherein the biological data for learning includes a hormone concentration value for learning of the learning subject, and the biological data for testing includes a hormone concentration value for testing of the test subject, and in the process (1),
after the 1_2th estimated mental health data for learning or the 1_2th GT mental health data, and the biological data for learning including the hormone concentration value for learning of the learning subject are input to the 1_3th estimated model, by referring to the 1_3th estimated mental health data for learning output from the 1_3th estimated model and the 1_3th GT mental health data, the 1_3th estimated model is learned.

16. The mental health estimating device of claim 15, wherein the hormone concentration value for learning includes a Cortisol concentration value for learning and a dehydroepiandrosterone (DHEA) concentration value for learning, and the hormone concentration value for testing includes a Cortisol concentration value for testing and a DHEA concentration value for testing.

17. The mental health estimating device of claim 16, wherein the hormone concentration value for learning further includes a sex hormone concentration value for learning, and the hormone concentration value for testing further includes a sex hormone concentration value for testing, and in the process (1),
when the sex hormone concentration value for learning meets a threshold range, in a state in which a first weight applied to the 1_1th positive psychological information for learning and the 1_2th positive psychological information for learning is set to be smaller than a second weight applied to the 1_1th negative psychological information for learning and the 1_2th negative psychological information for learning, the 1_1th estimated model to the 1_3th estimated model are learned.

18. The method of claim 16, wherein the estimated mental health data for testing includes information about the cortisol concentration value and the DHEA concentration value calculated by analyzing the first saliva for testing to the fourth test saliva sampled from the test subject, wherein the cortisol concentration value and the DHEA concentration value are resulted from measuring the cortisol concentration and the DHEA concentration based on saliva sampled before going to sleep, after waking up, 30 minutes after waking up, and 60 minutes after waking up, when the region corresponding to the cortisol concentration value and the DHEA concentration value calculated by analyzing the first saliva for testing to the fourth test saliva sampled from the test subject is region No. 9, the Cortisol concentration of the test subject is higher than the normal level, since the DHEA appears to be in the normal range or higher than the normal range in the low state, the mental health estimating device 1000 may output the estimated mental health data for testing that includes information on the effect that a comprehensive review is necessary because these results occurred due to biological diseases or artificially taken drugs, or saliva sampling was not performed accurately.

19. The mental health estimating device of claim 16, wherein the estimated mental health data for testing includes information about the cortisol concentration value and the DHEA concentration value calculated by analyzing the first saliva for testing to the fourth test saliva sampled from the test subject, wherein the cortisol concentration value and the DHEA concentration value are resulted from measuring the cortisol concentration and the DHEA concentration based on saliva sampled before going to sleep, after waking up, 30 minutes after waking up, and 60 minutes after waking up, when the region corresponding to the cortisol concentration value and the DHEA concentration value calculated by analyzing the first saliva for testing to the fourth test saliva sampled from the test subject is region No. 9, the Cortisol concentration of the test subject is higher than the normal level, since the DHEA appears to be in the normal range or higher than the normal range in the low state, the mental health estimating device 1000 may output the estimated mental health data for testing that includes information on the effect that a comprehensive review is necessary because these results occurred due to biological diseases or artificially taken drugs, or saliva sampling was not performed accurately.

20. The mental health estimating device of claim 15, wherein, by analyzing (i) first saliva for learning to fourth saliva for learning sampled at a first sampling time for learning to a third sampling time for learning that exists within a first threshold time range from a time when the learning subject wakes up, and at a fourth sampling time for learning that exists within a second threshold time range from a time when the learning subject goes to sleep, and (ii) first saliva for testing to fourth saliva for testing sampled at a first sampling time for testing to a third sampling time for testing that exists within the first threshold time range from the time when the test subject wakes up and at a fourth sampling time for testing that exists within the second threshold time range from the time when the test subject goes to sleep, respectively, each of the hormone concentration value for learning and the hormone concentration value for testing is calculated.

21. The mental health estimating device of claim 20, wherein the hormone concentration value for learning and the hormone concentration value for testing are respectively calculated by analyzing each of the first saliva for learning to the fourth saliva for learning and the first saliva for testing to the fourth saliva for testing through a radioimmunoassay.

22. The mental health estimating device of claim 14, wherein the biological data for learning includes a heart rate variability value for learning of the learning subject, and the biological data for testing includes a heart rate variability value for testing of the test subject, and in the process (1),
after the 1_2th estimated mental health data for learning or the 1_2th GT mental health data, and the biological data for learning including the heart rate variability value for learning of the learning subject are input to the 1_3th estimated model, by referring to the 1_3th estimated mental health data for learning output from the 1_3th estimated model and the 1_3th GT mental health data, the 1_3th estimated model is learned.

23. The mental health estimating device of claim 14, wherein the biological data for learning includes brain image data for learning and microbiome data for learning of the learning subject, and the biological data for testing includes brain image data for testing and microbiome data for testing of the test subject, and in the process (1),
after the 1_2th estimated mental health data for learning or the 1_2th GT mental health data, and the biological data for learning including the brain image data for learning and the microbiome data for learning of the learning subject are input to the 1_3th estimated model, by referring to the 1_3th estimated mental health data for learning output from the 1_3th estimated model and the 1_3th GT mental health data, the 1_3th estimated model is learned.

24. The mental health estimating device of claim 14, wherein the 1_1th psychological data for learning includes adult attachment type information for learning, adverse childhood experiences information for learning, and mind understanding ability information for learning of the learning subject, the 1_2th psychological data for learning includes depression scale information for learning and suicide risk information for learning of the learning subject,
the 1_1th psychological data for testing includes adult attachment type information for testing, adverse childhood experiences information for testing, and mind understanding ability information for testing of the test subject,
the 1_2th psychological data for testing includes depression scale information for testing and suicide risk information for testing of the test subject, and
in the process (1),
(i) after the 1_1th psychological data for learning including the adult attachment type information for learning, the adverse childhood experiences information for learning, and the mind understanding ability information for learning is input to the 1_1th estimated model, by referring to the 1_1th estimated mental health data for learning output from the 1_1th estimated model and the 1_1th GT mental health data corresponding to the 1_1th estimated mental health data for learning, the 1_1th estimated model is learned, and (ii) after the 1_1th estimated mental health data for learning or the 1_1th GT mental health data, and the 1_2th psychological data for learning including the depression scale information for learning and the suicide risk information for learning are input to the 1_2th estimated model, by referring to the 1_2th estimated mental health data for learning output from the 1_2th estimated model and the 1_2th GT mental health data corresponding to the 1_2th estimated mental health data for learning, the 1_2th estimated model is learned.

25. The mental health estimating device of claim 24, wherein at least a part of the 1_1th psychological data for learning and the 1_2th psychological data for learning further includes recovery resilience information for learning of the learning subject, and at least a part of the 1_1th psychological data for testing and the 1_2th psychological data for testing further includes recovery resilience information for testing of the test subject.

26. The mental health estimating device of claim 13, wherein in the process (1),
(i) after the psychological data for learning and the biological data for learning of the learning subject are input to the first estimated model, by referring to the estimated mental health data for learning output from the first estimated model and the GT mental health data, the first estimated model is learned, and (ii) after an estimated mental health data for learning or the GT mental health data is input to a second estimated model, by referring to (ii-1) post-treatment estimated mental health data for learning of a learning subject whose mental health status has been changed by applying at least a part of a drug treatment process and a psychotherapy process to the learning subject, (ii-2) estimated drug treatment data for learning for the drug treatment process, and (ii-3) estimated psychotherapy data for learning for the psychotherapy process, which are output from the second estimated model, and post-treatment GT mental health data, GT drug treatment data, and GT psychotherapy data corresponding to each of them, in a state in which the second estimated model is learned, the processor acquires the psychological data for testing and the biological data for testing of the test subject from the terminal of the test subject, in the process (2), the processor inputs the psychological data for testing and the biological data for testing to the first estimated model to allow the first estimated model to output the estimated mental health data for testing.

\* \* \* \* \*